(12) United States Patent
Benoit et al.

(10) Patent No.: US 7,193,075 B2
(45) Date of Patent: Mar. 20, 2007

(54) SEQUENCES UPSTREAM OF THE CARP GENE, VECTORS CONTAINING THEM AND USES THEREOF

(75) Inventors: Patrick Benoit, Paris (FR); Bertrand Schwartz, Jouy En Josas (FR); Didier Branellec, Brie-Comte-Robert (FR); Kenneth R. Chien, La Jolla, CA (US); Ju Chen, San Diego, CA (US)

(73) Assignees: Centelion (FR); The Regents of the University of California, Oakland, CA (US)

( * ) Notice: Subject to any disclaimer, the term of this patent is extended or adjusted under 35 U.S.C. 154(b) by 0 days.

(21) Appl. No.: 10/005,337

(22) Filed: Dec. 7, 2001

(65) Prior Publication Data

US 2003/0039984 A1    Feb. 27, 2003

Related U.S. Application Data

(60) Provisional application No. 60/251,582, filed on Dec. 7, 2000.

(51) Int. Cl.
| | |
|---|---|
| *C07H 21/02* | (2006.01) |
| *C07H 21/04* | (2006.01) |
| *A01N 43/04* | (2006.01) |
| *A61K 31/70* | (2006.01) |
| *C12N 15/00* | (2006.01) |

(52) U.S. Cl. ............... 536/24.1; 536/23.1; 514/44; 435/320.1

(58) Field of Classification Search ............ None
See application file for complete search history.

(56) References Cited

FOREIGN PATENT DOCUMENTS

| WO | WO 00/15821 | * | 9/1999 |
|---|---|---|---|
| WO | WO 00/15821 | * | 3/2000 |

OTHER PUBLICATIONS

Aihara et al., "*Homo sapiens* Cardiovascular-specific Cardiac Ankyrin Repeat Protein (CVARP) Gene. 5'-Flanking Region and Exon 1," EMBL Database Accession No. AF131884, Feb. 15, 2000.*

Kuo et al. Control of segmental expression of the cardiac-restricted ankyrin repeat protein gene by distinct regulatory pathway in murine cardigoenesis. Development, 1999 vol. 126:4223-4234.*

(Continued)

*Primary Examiner*—Sean McGarry
*Assistant Examiner*—Terra C. Gibbs
(74) *Attorney, Agent, or Firm*—Finnegan, Henderson, Farabow, Garrett & Dunner, LLP

(57) ABSTRACT

The invention relates to novel promoter sequences derived from a portion upstream of the coding sequence of the gene for the CARP protein (Cardiac Ankyrin Repeat Protein), and which are capable of controlling the level and the specificity of expression of a transgene in vivo in cardiac muscle cells. The invention thus describes novel compositions, constructs, vectors and their uses in vivo for the transfer and expression of a nucleic acid in vivo in cardiac muscle cells. The subject of the present invention is also the use of the promoter sequences for generating transgenic animals which constitute models for studying certain cardiac pathologies.

17 Claims, 8 Drawing Sheets

OTHER PUBLICATIONS

Figure 3:
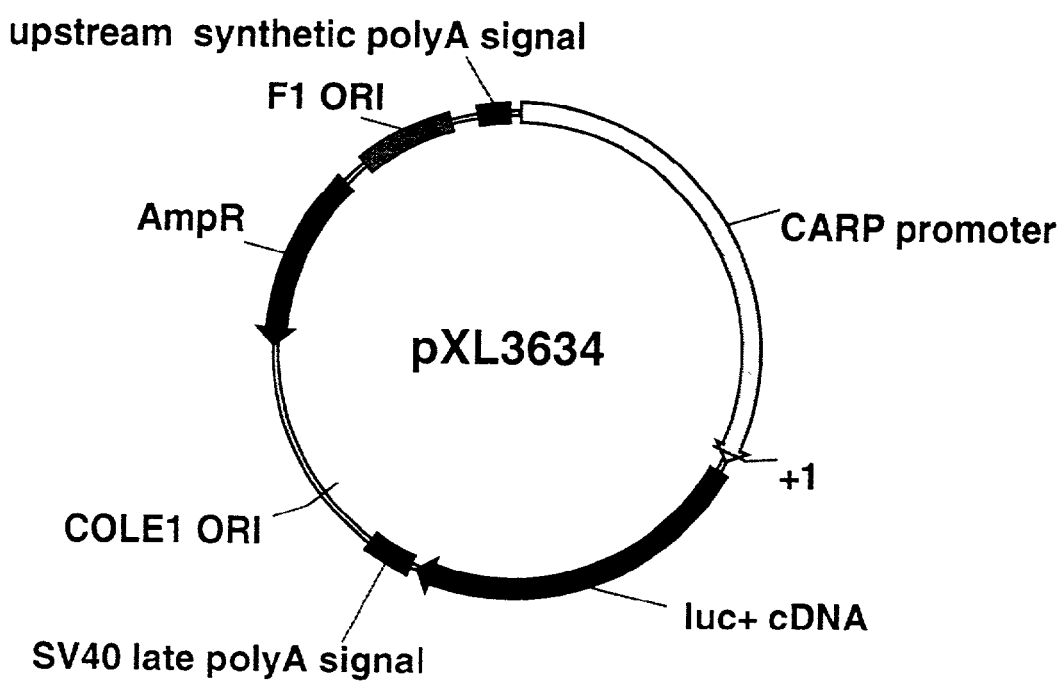

Alarco et al. The bZip Transcription factor Cap1p is involved in multidrug resistance and oxidative stress response in *Candida albicans*. Journal of Bacteriology, 1999 vol. 181:700-708.*

Mohuczy et al. Antisense inhbiiton of AT1 receptor in vascualr smooth muscle cells using deno-associated virus-based vector. Hypertension, 1999 vol. 33:354-359.*

Phillip et al. Gene Modification of Primary tumor cells for active immunotherapy of human breast and ovarian cancer. Clinical Cancer Research, 1996 vol. 2:59-68.*

Chen et al. Overexpression of human endothelial nitric oxide synthase in rat vascular smooth muscle cells and in balloon-injured carotid artery. Circulation Reseach, 1998 vol. 82:862-70.*

Aihara et al. "*Homo sapiens* Cardiovascular-Specific Cardiac Ankyrin Repeat Protein (CVARP) Gene, 5'Flanking Region and Exon 1," EMBL Database Accession No. AF131884, Feb. 15, 2000. See sequence alignment.*

Fu et al. Viral sequences enable efficient and tissue-specific expression of transgenes in Xenopus. Nature Biotechnology, 199 vol. 16:253-257.*

Hai-Chien et al., "Control of Segmental Expression of the Cardiac-Restricted Ankyrin Repeat Protein Gene by Distinct Regulatory Pathways in Murine Cardiogenesis," *Development*, vol. 126, pp. 4223-4234, 1999.

Jeyaseelan et al., "A Novel Cardiac-Restricted Target for Doxorubicin," *The Journal of Biological Chemistry*, vol. 272, 22800-22808, 1997.

Zou et al., "CARP, a Cardiac Ankyrin Repeat Protein, is Downstream in the Nkx2-5 Homeobox Gene Pathway," *Development*, vol. 124, 793-804, 1997.

* cited by examiner

FIGURE 1

```
   1 ggatccttc  atgtttaaca  atatcaaccc  taacccaagg  ggaacagcct  gcctgacagt
  61 ggctttgcca  cccatgaata  ctcctagtc   tagtccgttt  gtgaaactca  gcccatccca
 121 acacttctgc  aagccccatc  ctccacaagg  tgctcattgg  gaatttcctg  gagcttctct
 181 ttcaggatca  gcctgattct  agggcagcag  ttctcaacct  ggggcctcg   acccctttgg
 241 gggaatcaaa  cgacccttta  caggggtcac  atatcatcta  tcctatatgt  caggtattta
 301 cattacgatt  cgtaacagta  gcaaaattac  aggtatgaaa  tagcaatgaa  ataattttat
 361 gattgaaggt  caccacaaca  tgaggccgcc  acactgttct  agagaaaaat  cacctgggtg
 421 gggaaggtt   tgggaaagcc  tttctgtcca  ttcttcattc  ttcaaagtga  tgtgttcaca
 481 gaaagccttt  cagctgttct  gctggggctc  ttagtaagtc  tgagtaggaa  ctgtatgtac
 541 caggtctgct  tcttatgggt  ggagccaaga  cgcatcgtgg  gtggagcgaa  gacgcaacct
 601 caccttctag  ctctgcatcc  atagcaagta  gcctaatgtt  tctgtgtcta  ggtgtcatct
 661 ctgtgaatcg  agatccttgg  cctgcttga   attaggagg   cacaaaatac  tcagagattc
 721 aagactgctc  agcagcccag  agtccttcct  caaaggaaag  gtctcaactc  tcagcccccc
 781 ttagctctga  gtcaggcctg  gaacaaacgg  ccacaggaat  gagaaaagct  gccatagctg
 841 cttgtcactt  caagaggtca  aagaaaatag  tgttaaccat  gaaacgaga   agaccaacag
 901 ttatccattg  atagcgtctc  aggacagata  ggacagagag  aacactagga  gaggggaacc
 961 cacgaaggac  aaggtattag  tgtgttggtt  ttcagggcaa  tgtcttgtac  tgaagattct
1021 agaaacacaa  ttgctggtt   gaacagctga  agtgggtgg   gggttcttac  cccatgttca
1081 tggaaggtg   agtgaggaga  gacagatata  tgatggccag  cataacaaac  atacacaaca
1141 ccctaattaa  cacttccctc  ttctactgac  acccccttca  ctctcctctt  tcataaaaaa
1201 taaaaaaagt  attttatgtg  gctcttacga  tagaatcttt  cctcgaacta  taaaaagatc
1261 taaatattta  tatttttcac  attttaatat  cttagcgatg  acaagccaga  aacaagtatt
1321 ttttgcctct  ctcaacagca  aagcttgggg  cctttttgtt  tccgtgttag  gaatagaaca
1381 cgagagcccc  gtgtatctag  gcagatgctc  tatcattagc  ccatgagtct  ccagcctcag
1441 acgcacattt  ttctcgggct  ctcttaagct  tttcccacag  cattgggtgc  ctttactgac
1501 agcatccaag  ttgtgcttct  gctaagaact  ggactcacat  ctctctgtgc  atcacttcgg
1561 cccgttttgg  ggtagatcct  ctgattagcc  ttcagattta  gaacacggtg  agcctgtggt
1621 gcactaatta  tggccagtga  caccatagag  tcaaagtgca  ttactgaatg  ctttcaattt
1681 ctcctaatgc  tggtacgatg  gcatgtcaca  gggccatttt  agctgcagac  atcactccag
1741 agaattccaa  acagatagag  acaagtggca  cccagaccca  tctccttccc  ctcgggctga
1801 ttatcccag   aaataggatg  tcccaaagca  acacttccca  gccaactgga  gtgctgataa
1861 gtccagttat  cagaaagata  tggctgtaag  tgtgatgcac  agtgcttgca  ttttcttgat
1921 acgttagtca  tatgagagct  gacaagaag   gaaaagagc   agcgatgtgg  tgcaatatta
1981 acaggcagct  gtccctggc   ttcccgatac  gtgggatgac  tcgcattgct  gagcggtgtg
2041 gtcactgcca  aaggaatgac  cctctcacat  ttcttcctga  ttcgcatacg  ccgcggccag
2101 cttgtcatct  ccctccttggg ctcccagac   actaagtctg  gaatgaaaat  tcacctgcct
2161 ctgaattggc  cactggtggg  ggcagggtg   tgacttggct  tcccaggctg  gaagattatc
2221 tcacccagcc  ctagctatat  aacgggctgg  tgtggagggg  ctccacaggg  ccagttccag
2281 gggttcatcc  acaagagaga  aaaacataga  ctcgaggtct  agggagcttg  catgcctgca
2341 ggtcggaggc  caccatgg
```

FIGURE 2

```
   1 ctgcagcaag ttacttaatg ttttttgcct cagcatcctc tctgtaaaat gagagcatta
  61 gtcttgctcc aacttcgagg gcatggacag ctctgggatt tcatatccaa gacccttaaa
 121 catcccacag tccttccccc aaacacttct cctcctaata cctccctcag tttgggtcag
 181 gcctggaaca aaaaggcata cgaaatggta gaaaaagtgt ccatgactac ttctgactta
 241 gatgaagaga ccaatgaaaa tagtaatgac tctgtttgct tcagcaggac atatactaaa
 301 ataggagcta tacaaagaag attagcatgg actctgtgca agaatgacac acaaatttgt
 361 gaaacattcc atatattaaa aataaataaa taataaagag aaaaggaaaa aattaaaaag
 421 aaaatagtga tagctgtgtc catctcaaag aaaagcccag gagatttcct ttatttaccc
 481 cctttaagat agaatattag gagaccggaa catatgatac aggaggtact gggagggtcc
 541 ctctttgtca atgttttgtc ttggggtggg gagtcgatgt cttctcaaag tttcagaaac
 601 accatccact gactgagcat tcaaggggca agaggagaat ggcagccaca tttgttgatt
 661 gggtgagttt ggggagaaat agacacacaa aggtcaaaca taacttccta attaacactt
 721 ccctccattc acaattccct tctcccattc ttctctcctg tcttttacts akaraaaccc
 781 agtttttcct gaaactataa aaataccccc agtatgttta cataatttac acctcaaaga
 841 ttagaaacca gaaatagaga cctttcaac ccttccggaa gcaaagtgca ttatccctcc
 901 agccacgtgt ctcaaatctt gatgcatcag aatcatctgg gtgctttkaa attcaagatg
 961 attcctacga gttaccataa atcaactcag aattccctgg agtggggcca gggatctgta
1021 tttctgacaa gctcccacag gtgattcctt tccccacagc atttgagaac ttcagctcaa
1081 tgacctaatc agagtcctgc cattgctaat atctggtctc attttbtca tatatatata
1141 tagtatttgt ggtagagatg ggattttgcc atgttgccca ggctagtatt gaactcctaa
1201 gctaagcaat cttcctgtct ctgcctccca aaatgttggg attacaggtg taagccactg
1261 caccccggctg atagctggtt tcatttactc tatttcttga ccactctgat ccattttgaa
1321 gtaaaaatgc tccaattatt atgctgtttt agaacacggt aagcatgtca tgtgctaatg
1381 gccagtgaca tcataaaaga aaagtgcatt actgaatgct ttcaatgtct tataatgatg
1441 gtaaggtggc atgtcatggg gcctatttag cccagacatc actccaaaga attccaaaca
1501 gatatagaca agtgccttta gggcccagat cccttccct caggctgttt acccaggaa
1561 taggatgtcc tgggacaagt ttcccctaag tgaagtgttg ataagtctgc ttatcagaaa
1621 gatattactg ggggtgtgat atgtagggca tctacattt cttgataggt agtcatatga
1681 aagctgacaa agaaaaaaag ggcagtgatg tggtgcaatg tcaacagaca gctgtcccct
1741 gactcttgac aaataggatg acttgcattg ctgagcgatg tgatcaccac caaaggaatg
1801 gccctctcac atttcttcct gattcacata ttcagcaggg ttagcttgtc ctccctccc
1861 tcttcagctt cccagacact gagtctggaa tgaaaattca cctgcctctg agttggctcc
1921 taatggggc gggagtgtta cttcggttcc caggttggaa gattatctca cccggcccca
1981 gctatataag ctgaccggtg tggaggggcc cagcagggcc aactccaggg attccttcca
2041 cgacagaaaa acatacaaga ctccttcagc caac
```

SEQUENCES UPSTREAM OF THE CARP GENE, VECTORS CONTAINING THEM AND USES THEREOF

This application claims the benefit of U.S. Provisional Application No. 60/251,582, filed Dec. 7, 2000, which is incorporated herein in its entirety.

The present invention relates to the field of biology. It relates in particular to the field of the targeting of the expression of genes, and more particularly the design and the development of a novel system for the specific expression of transgenes. The subject of the invention is, in particular, novel promoter sequences capable of controlling the level and the specificity of expression of a transgene in vivo in cardiac muscle cells. The invention thus describes novel compositions, constructs and vectors that make it possible to control and to direct the expression of a nucleic acid in cardiac muscle cells. The applications stemming from the present invention are numerous, for example in the experimental, clinical, therapeutic and diagnostic fields, and more particularly for the treatment and/or prevention of certain cardiac pathologies.

The control of the level and of the targeting of the expression of transgenes is necessary for many applications. For example, in gene therapy the success of the therapy may require targeting of the protein synthesized from the transgene and thus make it possible to limit the spread of side effects. The construction of transgenic animals and the study of the effects of a gene are additional examples in which an appropriate control of the specificity of expression of a protein can be used and can provide improvements.

In this regard, many promoters have been tested for their capacity to direct a cardiospecific expression. They are in particular the promoters of the gene encoding the cardiac myosin light chain (MLC-2) in rats (Henderson S. A. et al., *J Biol Chem*, 264 (1989) 18142–8; Lee K. J. et al., *J Biol Chem*, 126 (1992) 15875–85), cardiac α-actin in mice (Biben C. et al., *Dev Biol*, 173 (1996) 200–12), atrial natriuretic factor (ANF) (Harris A. N. et al., *J Mol Cell Cardiol*, 29 (1997) 515–25), α- or β-myosin heavy chain (α- or β-MHC) (Colbert M. C. et al., *J Clin Invest*, 100 (1997) 1958–68), muscle creatine kinase (MCK) in rabbits (Vincent C. K. et al., *Mol Cell Biol*, 13 (1993) 567–74), or cardiac troponin T (U.S. Pat. No. 5,266,488).

While these promoters are known to confer a degree of tissue specificity, it is also known that their levels of activity remain well below those of so-called strong promoters, generally by a factor of between 10 and 100, such that a therapeutic use cannot really be envisaged.

By way of example, Franz W. M. et al., (*Cardiovasc Res*, 35 (1997) 560–6) and Griscelli F. et al., (*C R Acad Sci III*, 320 (1997) 103–12) have shown that the levels of activity of the sequences upstream of the genes encoding rat α-MHC and MLC-2 in adenoviral constructs remain substantially lower than those of the RSV (Rous sarcoma virus) promoter, by a factor of about 10.

The present application, therefore, relates to a novel promoter sequence derived from the region upstream of the CARP (Cardiac Ankyrin Repeat Protein) gene. This sequence is capable not only of directing a cardiospecific expression, but also exhibits a high level of expression in vivo, comparable to that of a strong promoter such as the CMV (cytomegalovirus) promoter.

The CARP protein, which constitutes one of the first markers for differentiation of cardiomyocytes acting downstream of the homeobox gene Nbx2.5 in the regulation of the expression of the MLC-2v gene, has been studied and the coding portion of its gene has been sequenced in mice (Zou Y. et al., *Development*, 24 (1997) 793–804), in rabbits (Aihara Y. et al., *Biochim Biophys Acta*, 28 (1999) 318–24), and in humans (Chu W. et al., *J Biol Chem*, 270 (1995) 10236-45).

Kuo H. et al. (Development, 126 (1999) 4223–34) have cloned a 10 Kb fragment and sequenced a 2.5 Kb fragment upstream of the coding sequence of the mouse CARP gene. Deletions from the 5'-end of the fragment were made and showed that a region of 213 bp of the promoter between nucleotides −166 and +47, relative to the transcription start position +1, was sufficient to confer cardiospecific expression in vitro, which suggested the presence, at the 5'-end, of an element for controlling the specificity of the promoter. Kuo et al. also generated transgenic mouse lines comprising a fragment of 2.5 Kb upstream of the CARP gene, showing specific expression of a transgene in cardiac and skeletal muscle cells at an early stage of embryonic development, this expression then being inhibited during development.

Application WO 00/15821 describes a portion 5' of the coding sequence of the mouse CARP gene, situated between nucleotides −2285 and +62, relative to the transcription start position +1. This sequence was evaluated in particular for its in vivo activity in adenoviral vectors. The levels of activity obtained remain very low, however, such that it was found to be necessary, in order to detect an activity in vivo, to isolate the promoter sequence between two inverted terminal repeats of an adeno-associated virus (AAV-ITR).

The Applicants focused on better characterizing the region upstream of the CARP gene protein-coding region. We were thus able to identify a novel sequence upstream of the CARP gene and demonstrate unexpected and advantageous properties of this novel sequence, in particular, a significant improvement in the level of activity in vivo.

The Applicants have discovered, surprisingly, that while this newly identified sequence conferred no significant expression in vitro, it was, on the contrary, possible to obtain very good levels of activity in vivo, equivalent to those of so-called strong promoters, while preserving a high selectivity for expression in cardiac tissue.

The subject of the present invention is therefore a polynucleotide comprising a portion upstream of the coding sequence of the gene for the CARP protein, or of a polynucleotide hybridizing under highly stringent conditions with said upstream sequence, the polynucleotide being capable of inducing specific expression in cardiac tissue of a transgene placed under its control.

The invention also relates to any polynucleotide of natural origin or which is obtained by chemical synthesis, exhibiting at least 93%, preferably at least 95%, identity with SEQ ID NO: 1. In a further embodiment of the invention, the polynucleotide exhibits at least 98% identity with SEQ ID NO: 1.

The term "polynucleotide of natural origin" is understood to mean a genomic DNA fragment obtained by cleaving cellular DNA with the aid of a restriction enzyme.

The term "polynucleotide obtained by chemical synthesis" is understood to mean a DNA fragment generated by automated or manual synthesis, for example, with the aid of a suitable automated apparatus.

For the present invention, the term "highly stringent conditions" is used in the sense given by Maniatis et al. 1982 (Molecular Cloning, A Laboratory Manual, Cold Spring Harbor CSH, N.Y., USA) or one of its more recent editions. By way of example, the hybridization conditions are such that three washes at 65° C. in the presence of 0.2×SSC, and 0.1% SDS are necessary in order to eliminate the nonhybridized fragments.

The "specific" character of transgene expression means that the activity of the promoter is significantly higher in cells of cardiac tissue. Although nonspecific expression can be observed in other cells, the corresponding level of activity remains very low (negligible) compared with that observed in cardiac cells, in general lower by a factor of at least 10.

The results presented in the examples show, in this regard, a difference in expression that may reach a factor of 1000, which reflects the high selectivity of the polynucleotides according to the invention for cardiac cells in vivo.

Moreover, the results presented in the examples below clearly show that the use of the polynucleotides of the invention offers a system for high levels of expression, above those for other promoters known to be specific for cardiac tissue, it being possible for the difference to exceed a factor of 100. These elements, therefore, illustrate the advantages and unexpected properties of the polynucleotide according to the invention, in terms of promoter strength and specificity, for the expression of nucleic acids of interest in the cardiac tissue.

Advantageously, the polynucleotide according to the invention comprises a portion of the sequence between −2266 and +92 (SEQ ID NO: 1), relative to transcription start position +1 of the CARP gene.

The subject of the present invention is therefore the sequences hybridizing, under high stringency conditions, with the sequence SEQ ID NO: 1.

The present invention is nevertheless not restricted to the polynucleotides containing fragments upstream of the mouse gene but relates to any functional variant or any other sequence of any other species having the same properties, namely being capable of specifically inducing expression in vivo of a transgene in cardiac tissue.

Thus, persons skilled in the art will be able to refer to the sequence upstream of the human gene deposited in GenBank under the reference AF131884 (SEQ ID NO: 2). The present invention thus encompasses any sequence comprising fragments of the sequences upstream of the gene for the CARP protein, modified, for example, by deletion of certain structures and which preserve identical or similar functions to that of the sequence SEQ ID NO: 1.

In one embodiment of the invention, the polynucleotide has at least 80% identity with SEQ ID NO: 2. In another embodiment of the invention, the polynucleotide has at least 90% identity with SEQ ID NO: 2.

The term "functional variant" is understood to mean any modified sequence preserving the properties of the polynucleotides as mentioned above. The modifications may comprise one or more additions, mutations, deletions and/or substitutions of nucleotides in the sequence considered. These modifications may be introduced by conventional molecular biology methods, such as, for example, site-directed mutagenesis, or by artificial synthesis of the sequence. The variants obtained are then tested for their capacity to mediate specific expression in cardiac muscle cells when compared to a polynucleotide having the sequence of SEQ ID NO: 1.

Another subject of the invention is an expression cassette comprising a polynucleotide as defined above operably linked to a transgene such that the expression of the latter is specifically directed in cardiac muscle.

An expression cassette according to the invention may also comprise a signal for the termination of transcription at the 3'-end of the nucleotide sequence of the transgene.

In one embodiment, the transgene comprises a nucleic acid encoding a protein or an RNA of therapeutic interest, which may, for example, be involved in cardiac pathologies such as cardiac insufficiency, cardiac hypertrophy, hypoxia, ischemia, or in cardiac transplant rejection.

As proteins of therapeutic interest, there may be mentioned, inter alia:

proteins inducing angiogenesis, such as, for example, members of the vascular endothelial growth factor (VEGF) family, members of the fibroblast growth factor (FGF) family and, more particularly, FGF1, FGF2, FGF4, FGF5, angiogenin, epidermal growth factor (EGF), transforming growth factor (TGF) α, TGFβ, tumor necrosis factor (TNF), Scatter Factor/hepatocyte growth factor (HGF), members of the angiopoietin family, cytokines and interleukins including IL-1, IL-2, IL-8, angiotensin-2, tissue plasminogen activator (TPA), urokinase (uPA), and molecules involved in the synthesis of active lipids (e.g., prostaglandins, Cox-1);

proteins involved in the control of cardiac contractility, such as phospholamban, phospholamban inhibitors, sarco-endoplasmic reticulum Ca(2+) ATPase-2a (SERCA-2a), β2-adrenergic receptor, and dystrophin or minidystrophin (FR91 11947);

proteins with cryoprotective activity, which block apoptosis, such as proteins which are members of the bcl family, and protein kinases such as AKT/PKB;

transcription factors, including, for example, natural or chimeric nuclear receptors, comprising a DNA-binding domain, a ligand-binding domain, and a transcription activating or inhibiting domain, such as, for example, the fusion proteins tetR-NLS-VP16, the fusion proteins derived from estrogen receptors, the fusion proteins derived from steroid hormone receptors, the fusion proteins derived from progesterone receptors, and the proteins of the CID (Chemical Inducer of Dimerization) system described by Rivera et al., (Rivera et al., *Nature Medicine*, 2 (1996) 1028–1032). There may be mentioned, in particular, as chimeric nuclear receptors, the nuclear receptors PPAR (Peroxisome Proliferator Activated Receptor) and PPAR2, as described in Applications WO 96/23884 and FR 99 07957, and by Frohnert et al., (*J Biol Chem* 274 (1999) 3970–3977), and by Mukherjee et al., (*J Biol Chem* 272 (1997) 8071–8076), either in its native form, without modification of the primary structure, or a modified PPAR2 comprising one or more ligand-binding sites or E/F domains (Schoonjans et al. *Biochim. Biophys. Acta.* 1302 (1996) 93–109), such as PPAR22 having the sequence of SEQ ID NO: 3;

immunosuppressors such as, for example, interleukins 2 and 10 that make it possible to completely or partially inhibit an immune signaling pathway and, thus, to extend the duration of cardiac transplants;

proteins involved as agents for reducing hypoxia, such as NOS (nitric oxide synthetase), B-cell leukemia/lymphoma 2 (bcl-2), superoxide dismutase (SOD) and catalase.

As RNAs of therapeutic interest, there may be mentioned, for example, antisense RNAs, which are useful for controlling the expression of genes or the transcription of cellular mRNAs, thus blocking translation into a protein according to the technique described in Patent EP 140 308, as well as ribozymes that are capable of selectively destroying target RNAs as described in EP 321 201.

It is understood that the present invention is not limited to these specific examples of proteins or RNAs, but that it can be used by persons skilled in the art for the expression of any nucleic acid in cardiac cells by simple, customary, experimental operations.

The subject of the present invention is additionally a vector containing the polynucleotide or the expression cassette according to the invention. Such a vector may contain any other DNA sequence necessary or useful for the expression of the transgene in target tissues and, in particular, may contain a replication origin that is effective in the cardiac cells.

The vector of the invention may be of various natures and/or origins, for example, plasmid, cosmid, episomal, chromosomal, viral, or phage,. In one embodiment, the vector is either a plasmid or a recombinant virus.

By way of illustration of the plasmids according to the invention comprising a polynucleotide or an expression cassette, there may be mentioned, for example, the plasmids pXL3634, pXL3728 and pXL3759, which are described below.

According to one embodiment, the vectors according to the invention are of the plasmid type. As plasmid vectors, there may be mentioned, inter alia, any cloning and/or expression plasmids known to a person skilled in the art, which generally comprise an origin of replication. There may also be mentioned new-generation plasmids carrying replication origins and/or markers that have been refined, as described, for example, in Application WO 96/26270.

According to another embodiment, the plasmid vector is a miniplasmid and comprises an origin of replication whose functionality in the host cell requires the presence of at least one protein that is specific and foreign to the cell. Such vectors are described, for example, in Application WO 97/10343.

According to another embodiment, the vectors according to the present invention are viral vectors. Among the latter, there may be mentioned, inter alia, recombinant adenoviruses, recombinant adeno-associated viruses, recombinant retroviruses, lentiviruses, herpesviruses, and vaccinia viruses, whose preparation may be carried out according to methods known to persons skilled in the art. Chimeric viral vectors may be used, such as the adenovirus-retrovirus chimeric vectors that are described, inter alia, in Application WO 95/22617, as well as the episome/adenovirus vectors that are described by Leblois et al. (*Mol Ther*(2000) 1(4), 314–322) and in Application WO 97/47757.

When adenoviruses are used according to this embodiment, these are preferably vectors derived from defective adenoviruses, that is to say that they are incapable of autonomously replicating in the target cell. The construction of these defective viruses as well as their infectious properties have been widely described in the literature (see e.g., S. Baeck and K. L. March, *Circul. Research*, 82, (1998) 295–305; T. Shenk, B. N. Fields, D. M. Knipe, P. M. Howley et al. (1996), Adenoviridae: Viruses and Replication (in virology) 211–2148, EDS—Raven Publishers, Philadelphia; Yeh, P. et al. *FASEB* 11 (1997) 615–623).

Various adenovirus serotypes, whose structure and properties vary somewhat, have been characterized. Among these serotypes, use may be made in the context of the present invention, for example, of the type 2 or type 5 human adenoviruses (Ad 2 or Ad 5), or adenoviruses of animal origin, such as those described in Application FR 93 05954, or adenoviruses of mixed origin. Among the adenoviruses of animal origin that may be used in the context of the present invention, there may be mentioned the adenoviruses of canine, bovine, murine (Beard et al., *Virology* 75 (1990) 81), ovine, porcine, avian or simian origin. In one embodiment, the adenovirus of animal origin is a canine adenovirus, which may, for example, be a CAV2 adenovirus (Manhattan or A26/61 strain) as described in Application WO 94/26914.

The defective adenoviruses of the invention generally comprise an inverted terminal repeat (ITR) at each end, a sequence allowing encapsidation (Psi), the E1 gene, with at least one of the genes E2, E4 and L1–L5 having been inactivated by any technique known to persons skilled in the art (Levero et al., *Gene*, 101 (1991) 195, EP 185 573; Graham, *EMBO J.* 3 (1984) 2917).

In one embodiment, the recombinant adenovirus used in the invention comprises a deletion in the E1 region of its genome. This deletion may, for example, comprise a deletion of the E1a and E1b regions. By way of a specific example, there may be mentioned deletions affecting nucleotides 454–3328, 382–3446 or 357–4020 (with reference to the genome of Ad5).

According to another embodiment, the recombinant adenovirus used in the invention comprises, in addition to a deletion in the E1 region, a deletion in the E4 region of its genome. More particularly, the deletion in the E4 region affects all the open reading frames. There may be mentioned, by way of a specific example, deletion of nucleotides 33466–35535 or 33093–35535, again with reference to the genome of Ad5. Other types of deletions in the E4 region are described in applications WO 95/02697 and WO 96/22378, which are incorporated by reference into the present application.

Adeno-associated viruses (AAV) are relatively small-sized DNA viruses, which integrate into the genome of infected cells in a stable and site-specific manner. AAV can infect a broad spectrum of cells without having any effect on cell growth, morphology or differentiation. Moreover, AAV does not appear to be involved in pathologies in humans. The AAV genome has been cloned, sequenced and characterized. It comprises about 4700 bases and contains, at each end, an inverted terminal repeat (ITR) of about 145 bases, which serves as an origin of replication for the virus. The remainder of the genome is divided into 2 essential regions carrying the encapsidation functions: the left portion of the genome, which contains the rep gene involved in viral replication and in the expression of the viral genes, and the right portion of the genome, which contains the cap gene encoding the virus capsid proteins.

The use of AAV-derived vectors for the transfer of genes in vitro and in vivo has been described in the literature (see in particular WO 91/18088; WO 93/09239; U.S. Pat. Nos. 4,797,368, 5,139,941, EP 488528). These patent applications describe various AAV-derived constructs in which the rep and/or cap genes have been deleted and replaced with a gene of interest, and the use of these constructs for transferring in vitro (into cells in culture) or in vivo (into cells in an organism) the gene of interest. The defective recombinant AAVs according to the invention may be prepared by co-transfection transfection, into a cell line infected with a human helper virus (for example, an adenovirus), of a plasmid containing the nucleic sequences of the invention bordered by two AAV inverted terminal repeats (ITR) and of a plasmid carrying the AAV encapsidation genes (rep and cap genes). The recombinant AAVs produced are then purified by conventional techniques.

Lentiviruses also may be used in the invention. They allow the transfer and the efficient and stable integration of a gene of interest into quiescent cells. There may be mentioned, for example, HTLV-1 and animal lentiviruses, such as FIV (feline infections virus), EIAV (equine infectious anemia virus; WO 98/51810), BIV (bovine immunodeficiency virus), SIV (simian immunodeficiency virus), CAEV (caprine arthritisencephalitis virus) (WO 98/39463; Naldini et al. *Science* 272 (1996) 263–267; Schnele et al. *Hum Gen Ther* 11 (2000) 439–447), or a lentivirus related to the one that causes AIDS, HIV-2, which is not highly pathogenic in humans (Kundra et al., *Hum Gen Ther* 9 (1998) 1371–1380).

The expression cassette may be inserted at various sites of the recombinant genome. It may be inserted in the E1, E3, or E4 region, as a replacement for suppressed or surplus sequences. It may also be inserted at any other site, outside of the sequences necessary in cis for the production of the viruses (ITR sequences and the encapsidation sequence).

It will be noted, however, that the introduction of the sequences according to the present invention into the vectors described above is not essential. That is, cardiac cells may be directly transfected with DNA comprising these sequences.

The nucleic sequences according to the present invention may be introduced after covalent coupling of the nucleic acid to compounds that promote their penetration into cells or their transport to the nucleus, the resulting conjugates being, optionally, encapsidated into polymeric microparticles, as in International Application WO 94/27238.

According to another embodiment, the nucleic sequences of the invention may be included in a transfection system comprising polypeptides promoting their penetration into cells, as in International Application WO 95/10534.

The polynucleotides, cassettes and vectors of the invention may be administered in situ by any means known to persons skilled in the art, for example, by coronary infusion (Barr et al., *Gene Ther,* 1, (1994) 51–58), by intracardiac injection, by epicardiac injection, that is to say through the ventricular wall (Guzman et al., *Cir Res,* 73 (1993) 1202–1207), by intrapericardiac injection (Fromes et al., *Gene Ther,* 6 (1999) 683–688), or by retrofusion of the coronary veins (Boeckstegers et al., *Circulation,* 100 (Suppl I) (1999), I-815).

The polynucleotides, cassettes, or vectors according to the invention may be administered as part of a composition containing them, for example, with the aid of a chemical or biochemical transfer agent facilitating their transfection into cardiac cells. The phrase "chemical or biochemical transfer agent" is understood to mean any compound facilitating the penetration of a nucleic acid into a cell. This may include cationic agents such as cationic lipids, peptides, polymers (Polyethylenimine, Polylysine), nanoparticles, and non-cationic agents, such as non-cationic liposomes, non-cationic nanoparticles, or polymers. Such agents are well known to persons skilled in the art and are, for example, described in applications WO 95/18863, WO 97/18185 and WO 98/15639.

The present invention, in addition, relates to medicaments containing such polynucleotides, expression cassettes or vectors, as well as to pharmaceutical compositions containing them in a pharmaceutically-effective quantity, as well as pharmaceutically-compatible excipients.

Such polynucleotides, expression cassettes, or vectors may be used for the manufacture of medicaments for delivery to cardiac tissue, which may express a gene encoding a protein of interest for the treatment of cardiac diseases, for example, for the treatment and/or prevention of cardiac insufficiency, hypoxia, cardiac hypertrophy, myocarditis, cardiac ischemia, or for preventing rejection after cardiac transplant.

Such a medicament may, for example, comprise a cassette or vector according to the invention that is capable of expressing the functional form of an impaired gene according to the cardiac pathology that it is desired to treat.

Preferably, the pharmaceutical composition contains pharmaceutically-acceptable vehicles for an injectable formulation, for example, for intracardiac injection. This may include, for example, isotonic, sterile saline solutions (monosodium or disodium phosphate, sodium, potassium, calcium or magnesium chloride, and the like, or mixtures of such salts), or dry, for example, freeze-dried, compositions, which, upon addition of sterilized water or of physiological saline, as appropriate, allow the preparation of injectable solutions. Other excipients may be used, such as, for example, a hydrogel. This hydrogel may be prepared using any biocompatible and non-cytotoxic (homo or hetero) polymer. Such polymers have been described, for example, in application WO 93/08845. Some of them, such as those obtained from ethylene and/or propylene oxide, are commercially available. The doses used for the injection may be adjusted according to various parameters and according to the aim pursued (labeling, pathology, screening, etc.), the transgene to be expressed, or the duration of expression desired.

In general, the recombinant adenoviruses according to the invention are formulated and administered in the form of doses of between $10^4$ and $10^{14}$ pfu, and, preferably, between $10^6$ and $10^{10}$ pfu. The term pfu (plaque forming unit) corresponds to the infectious power of a viral solution, and is determined by infecting an appropriate cell culture, and measuring the number of plaques of infected cells. The techniques for determining the pfu titer of a viral solution are well known in the art.

The subject of the present invention is, in addition, a method of expressing a transgene of therapeutic interest during which the polynucleotides, cassettes or vectors according to the present invention are used, such that the transgene can be expressed.

Moreover, the invention also relates to any cell modified with a cassette or a vector (e.g., an adenovirus) as described above. The expression "modified" cell is understood to mean any cell containing a polynucleotide or a cassette according to the invention. Modified cells may be intended for implantation into an organism, according to the methodology described in application WO 95/14785. These cells may be, for example, human cardiac cells.

The present invention also relates to transgenic animals, for example, mice carrying a polynucleotide or a cassette as defined above in which the gene encoding the protein of therapeutic interest is replaced with a reporter gene. Such transgenic mice may be used to screen molecules for their activity on the regulatory sequences of the gene encoding the CARP protein. Molecules may be administered to mice and, after sacrificing, histological sections may be prepared in order to identify the tissues stained with the reporter gene.

The transgenic animals according to the present invention also constitute molecular biology study means for understanding the molecular mechanisms underlying cardiac pathologies of genetic origin, such as cardiac insufficiency, cardiac hypertrophy, cardiac hyperplasia, and myocardial infarction. By way of example, there may be mentioned murine models for studying myocarditis in which the gene encoding interferon-1 (IFN-1) is inactivated (Aitken et al., *Circulation,* 90 (1994) 1–139).

Other animal models of interest according to the present invention may comprise the polynucleotide according to the invention linked to transgenes such as protooncogenes or oncogenes, for example, c-myc, thus constituting models of hyperplasia (Jackson et al., *Mol Cell Biol,* 10 (1990)

3709–3716), p21-ras for models of ventricular hypertrophy (Hunter et al., *J Biol Chem,* 270 (1995) 23176–23178), and the nuclear antigen of the Epstein-Barr virus for studying certain cardiomyopathies (Huen et al., *J Gen Virol,* 74 (1993)1381–11391).

According to another embodiment, the transgenic animals according to the invention are experimental models of cardiac hypertrophy and comprise an expression cassette in which the transgene encodes for example calmodulin (Gruver et al., *Endocrinology,* 133 (1993) 376–388), interleukin-6 or the interleukin-6 receptor (Hirota et al., *Proc Natl Acad Sci. USA,* 92 (1995) 4862–4866), cardiotrophin-1 (Pennica et al., *Proc Natl Acad Sci. USA,* 92 (1995) 1142–1146), and, finally, the α-adrenergic receptor (Milano et al., *Proc Natl Acad Sci. USA,* 92 (1994) 10109–10113).

Additionally, the polynucleotides according to the invention, modified to allow an increase in the expression of the CARP gene, also form part of the invention. The transgenic animals thus obtained constitute experimental tools for myocardial infarction (Stanton et al., *Circul Res,* 86 (2000) 939–945).

To carry out the present invention, a person skilled in the art can advantageously refer to the following manual: Sambrook et al. (Molecular Cloning, A Laboratory Manual, Cold Spring Harbor Laboratory Press, New York 1989), or one of its recent editions.

The present invention is described in greater detail with the aid of the following examples, which should be considered as illustrative and nonlimiting.

Legends to the Figures

Figure 4:
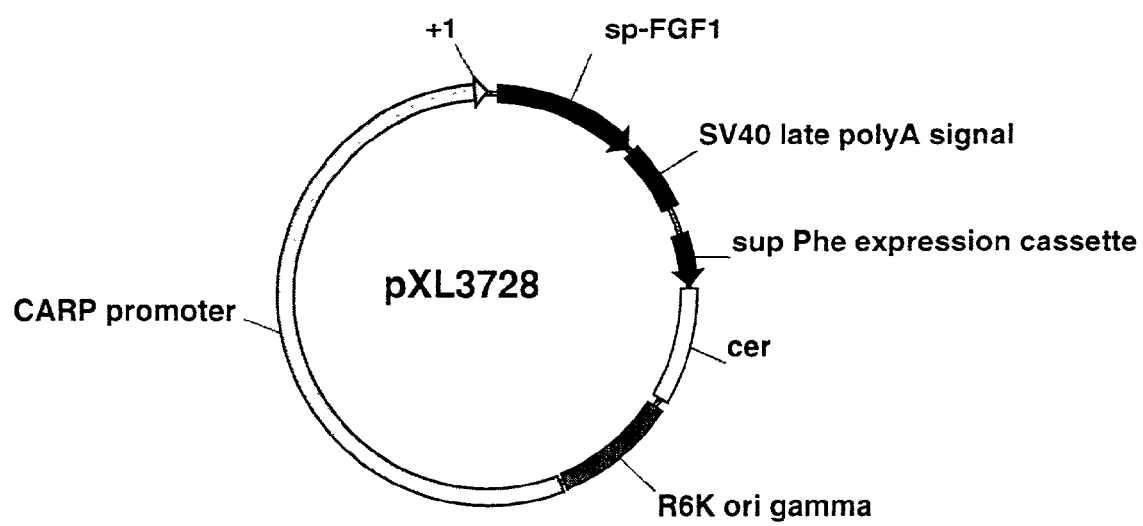
Figure 5:
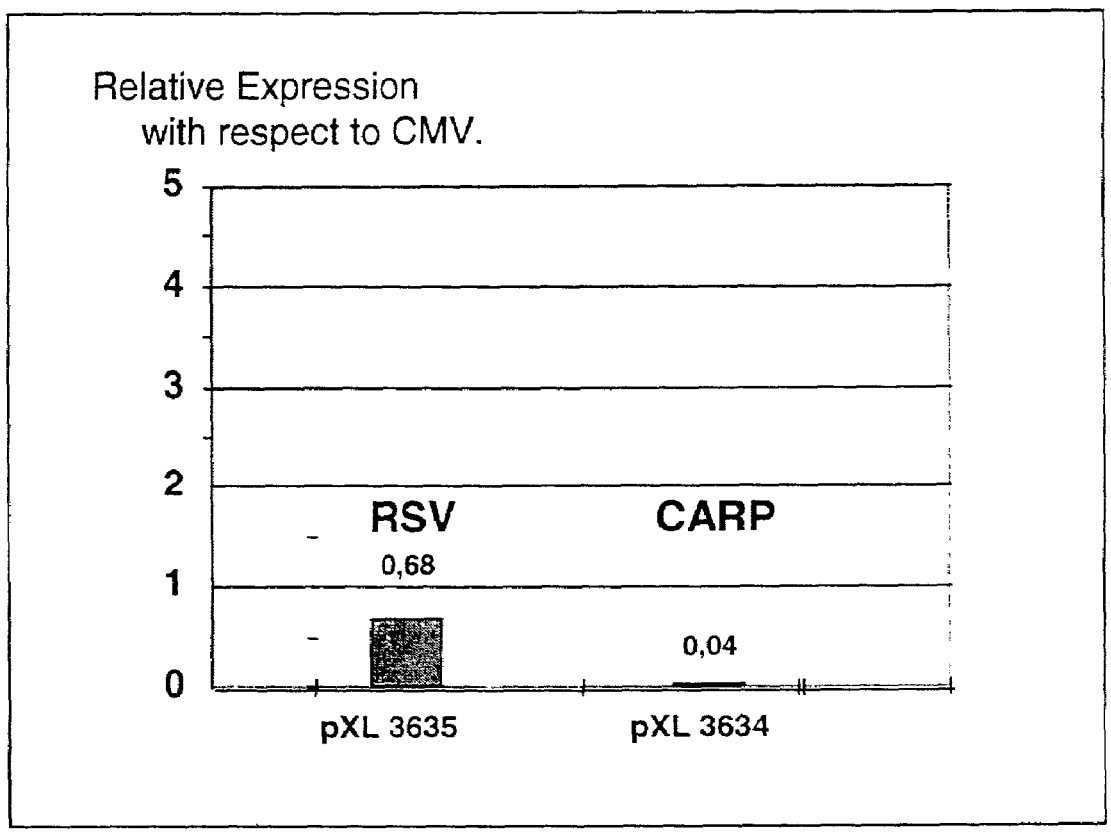

FIG. 1: illustrates the nucleotide sequence (SEQ ID NO: 1) of the polynucleotide upstream of the gene encoding the mouse CARP protein;

FIG. 2: illustrates the nucleotide sequence (SEQ ID NO: 2) of the polynucleotide upstream of the gene encoding the human CARP protein;

FIG. 3: is a schematic representation of the plasmid pXL3634;

FIG. 4: is a schematic representation of the plasmid pXL3728;

FIG. 5: illustrates the relative activity in vitro of the plasmids pXL3635 and pXL3634 with respect to the reference activity of the CMV promoter (pRL-CMV). The activity of each promoter is expressed as the *Photinus pyralis* luciferase activity normalized with the *Renilla reniformis* luciferase activity.

Figure 6A:
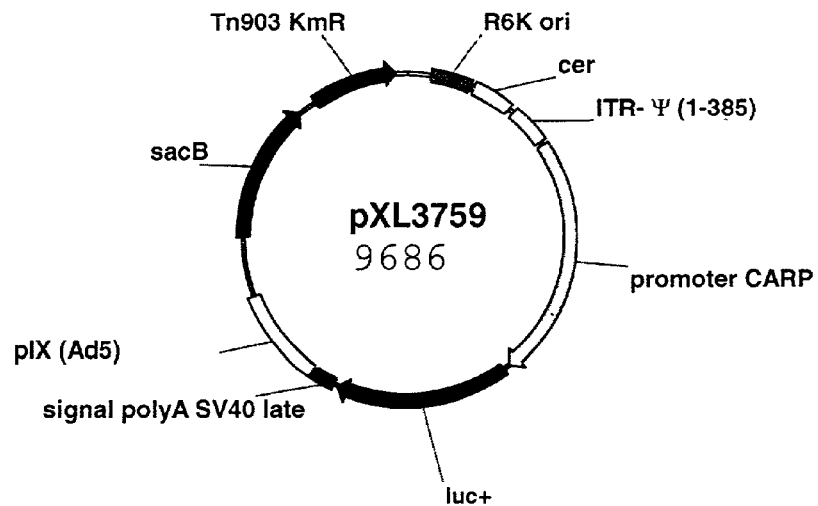
Figure 6B:
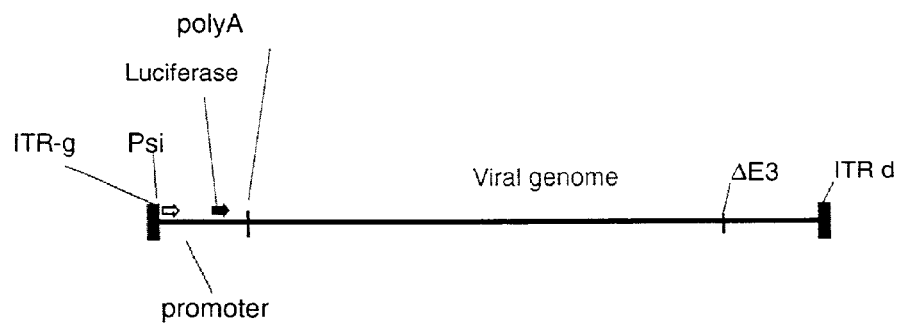
Figure 7A:
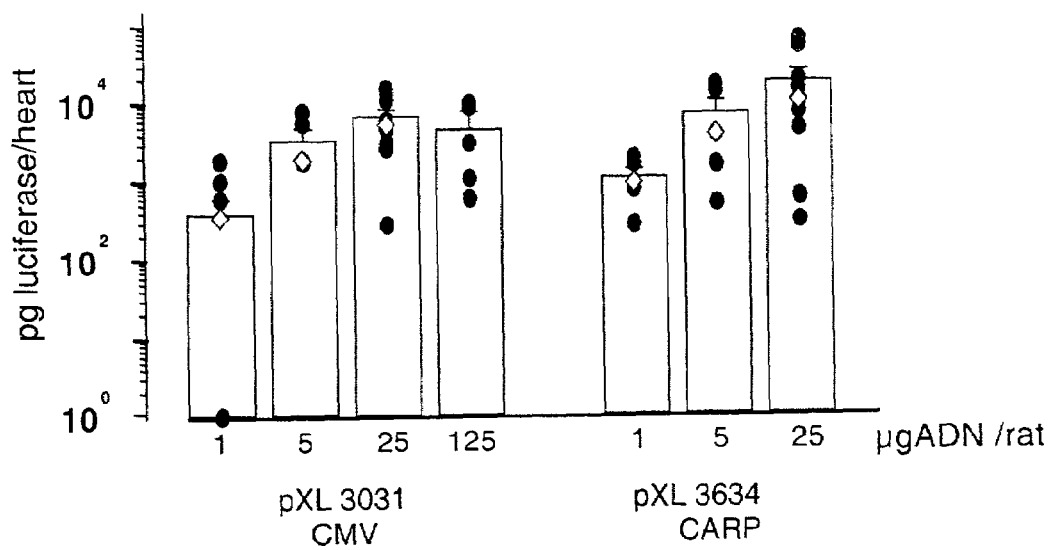
Figure 7B:
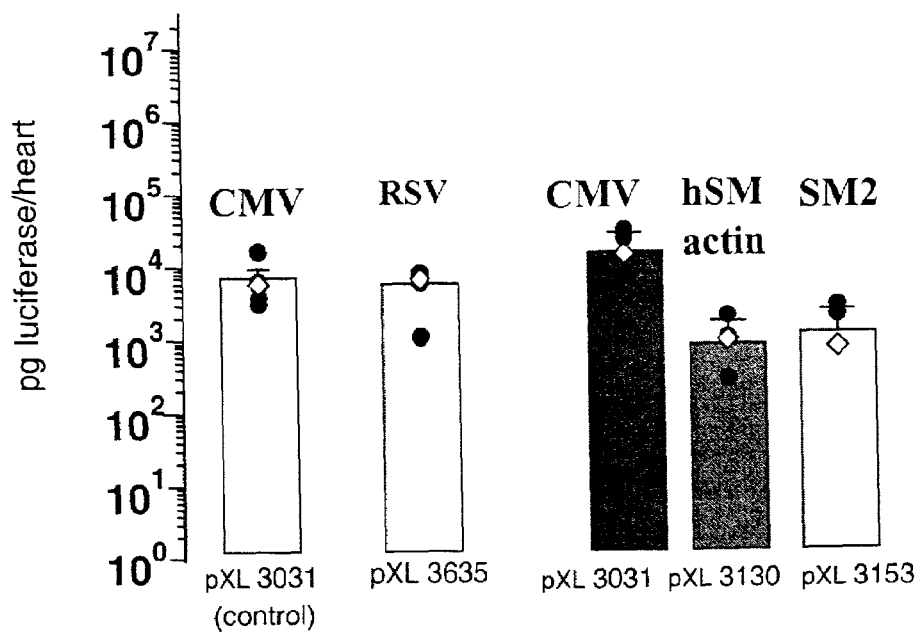

FIG. 6A: is a schematic representation of the plasmid pXL3759;

FIG. 6B: is a schematic representation of the adenovirus AV1.0 CARP-Luc+;

FIG. 7A: illustrates the luciferase activity (pg luciferase/ heart) 7 days after intracardiac transdiaphragmatic injection in rats of variable quantities of plasmids pXL3031 and pXL3634;

FIG. 7B: illustrates the luciferase expression (pg luciferase/heart) 7 days after intracardiac transdiaphragmatic injection in rats hearts of 25 g of plasmids pXL3031 and pXL3635, pXL3130, and pXL3153.

Figure 8:
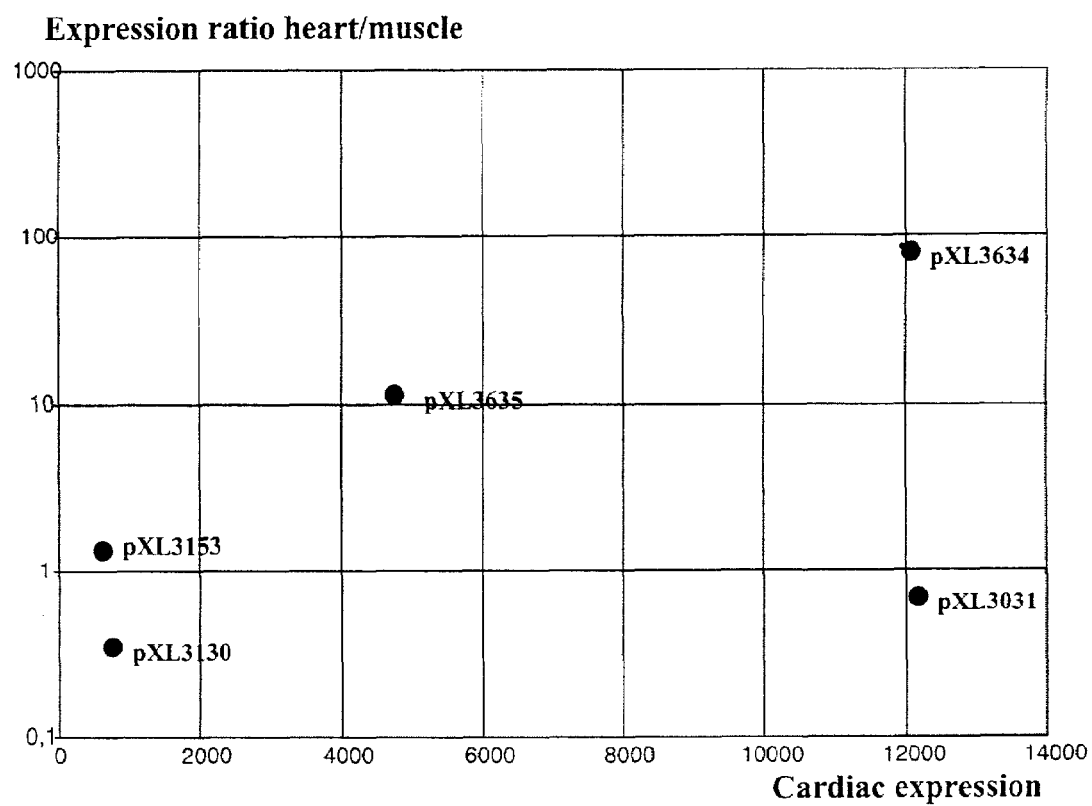

FIG. 8: represents the ratio of the expression of luciferase in the heart relative to the expression in the muscle as a function of the expression in the heart obtained following intracardiac administrations of plasmids pXL3031, pXL3634, pXL3635, pXL3153, and pXL3130.

EXAMPLES

Example 1

Characterization of the Polynucleotide Upstream of the CARP Gene

A BamHI-XhoI fragment of 2.3 Kb of the sequence at the 5'-end of the mouse gene encoding the CARP protein was cloned and sequenced on both strands according to the chain termination method (Sanger et al., 1977, *Proc. Natl Acad. Sci. USA,* 74, 5463) using the Sequenase® kit (United States Biochemical, Cleveland, Ohio). The sequence (SEQ ID NO: 1) is represented in FIG. 1 and comprises a portion upstream of the gene encoding the mouse CARP protein between nucleotides −2266 and +92 relative to transcription start position +1.

Example 2

Construction of CARP Plasmid Vectors 2.1 Plasmid pXL3634

The BamHI-XhoI fragment of 2.3 Kb characterized in Example 1 was cloned after filling in the BamHI site into the plasmid pGL3-Basic (Promega), which had been digested with XhoI and SmaI, in order to obtain the plasmid pXL3634. A schematic representation of this plasmid is presented in FIG. 3.

2.2 Plasmid pXL3728

The plasmid pXL3728 was obtained from the plasmid pXL3179, which was derived from the plasmid pXL2774 (WO 97/10343) in which the gene encoding a fusion between the signal peptide of human fibroblast interferon and the cDNA of FGF1 (fibroblast growth factor 1) (sp-FGF1, Jouanneau et al., *Proc. Natl. Acad. Sci USA* 88 (1991), 2893–2897) was introduced under the control of the promoter obtained from the human cytomegalovirus early region (hCMV IE) and the polyadenylation signal of the SV40 virus late region (GenBank SV4CG).

The BamHI-XhoI fragment of 2.3 Kb characterized in Example 1, whose ends have been filled in, was cloned into the plasmid pXL3179 (PCOR CMV-FGF), previously digested with XbaI and EcoRI, in order to obtain the plasmid pXL3728. A schematic representation of this plasmid is presented in FIG. 4.

2.3 Plasmid pXL3729

An EcoRI-SalI fragment of the plasmid pXL3634 was cloned into the plasmid pXL3728 previously digested with EcoRI-SalI in order to obtain the plasmid pXL3729.

Example 3

Comparative Plasmids 3.1 Plasmids pXL3130 and pXL3153

Plasmids pXL3130 and pXL3153 contain, respectively, the human smooth muscle α-actin promoter (−680 to +30) and the mouse SM22 promoter (−436 to +43) coupled to the CMV enhancer (−522 to −63) as described in application WO 00/18908.

3.2 Plasmid pXL3635

The RSV −229 to +34 promoter was cloned from a construct containing a longer version of the RSV promoter (contained in Ad1.0RSVLAcZ, Strafford-Perricaudet et al., *J Clin Invest* 90 (1992) 626–30) by PCR using of the primers 5'-GGC GAT TTA AAT AAT GTA GTC TTA TGC AAT-3' (SEQ ID NO: 4) and 5'-GGG GTC TAG AAG GTG CAC ACC AAT GTG GTG A-3' (SEQ ID NO: 5), which introduce, respectively, an SwaI and XbaI site at the 5'- and 3'-ends of the PCR fragment. These two restriction sites were then used to introduce the promoter fragment into pGL3-basic to generate pXL3635.

3.2 Plasmid pXL3031

The plasmid pXL3031 is described by Soubrier et al., *Gene Ther.* 6 (1999), 1482–8. It is a vector derived from the plasmid pXL2774 (WO 97/10343) in which the luc gene encoding the modified *Photinus pyralis* luciferase (cytoplasmic) obtained from pGL3basic (GenBank: CVU47295) was introduced under the control of the promoter obtained from the human cytomegalovirus early region (hCMV IE, GenBank HS5IEE) and of the polyadenylation signal of the SV40 virus late region (GenBank SV4CG).

Example 4

Cell Cultures

In order to establish primary cultures of rat cardiomyocytes, gestating rats were killed in a chamber saturated with $CO_2$. After opening the abdomen, the uterine horns were removed and washed in PBS at room temperature. The embryos were released from their envelopes and the placenta cut (10 to 12 embryos per rat). The hearts were removed and washed in ADS/glucose. Under a binocular lens, the auricles and large vessels were removed, and then the hearts were again cleaned in ADS/glucose so as to retain only the ventricles and then rinsed 3 times in sterile ADS/glucose.

The hearts were then trypsinized in 0.3 ml of an ADS/glucose/trypsin mixture per heart, using trypsin T 4674 (Sigma, St Louis, Mo.) at a final concentration of 0.1 mg/ml, for 20 min at 37° C., with gentle stirring (60 to 100 revolutions per min).

The supernatant was removed and the trypsin was inactivated by adding 1 ml of decomplemented fetal calf serum (FCS). After centrifugation at 1500 rpm for 10 minutes, the supernatant was removed and the cardiac cells were taken up in 1 ml of decomplemented FCS. In parallel, the steps of treating with trypsin were repeated 5 to 6 times until complete dissociation of the cells was obtained. The pool of cells was centrifuged at 1500 rpm for 10 minutes, then washed twice in FCS and the cells were finally filtered on a grid filter.

The cells thus separated were placed in culture at a concentration of $10^6$ cells/well for a 24-well plate or at a concentration of $2\times10^6$ cells/well for a 12-well plate. Each well contained 1 ml of culture medium.

The culture medium comprises, for a total volume of 100 ml, 68 ml of DMEM (without pyruvate) (Gibco-BRL), 17 ml of M199 (Sigma M 4530), 10 ml of decomplemented horse serum (Sigma H6762), 5 ml of decomplemented FCS (Gibo-BRL) and 1 ml of 100×Pen/Strep/glutamine mixture (Gibco-BRL).

The cardiomyocytes were cultured for a period of about 1 or 2 days.

Example 5

Transfection of Primary Cultures of Cardiomyocytes

The primary cultures of cardiomyocytes were cotransfected with a total quantity of DNA equal to 500 ng per well, comprising 1 ng of a plasmid pRL-CMV (Promega Inc., Madison, Wis.), variable quantities ranging from 1 to 100 ng of each of the plasmids pXL3635 and pXL3634 as described above, qs 500 ng of pUC19.

For that, the mixture of the plasmids was incubated with 6 nmol of RPR 120535B (Byk et al., *J Med Chem.* 41 (1998) 229–35) per µg of DNA (0.3 µl of solution of lipid at 10 mM) in a final volume of 20 µl in 150 mM NaCl, 50 mM bicarbonate, and then vortex-mixed for 5 seconds, and again incubated for about 20 to 30 minutes at room temperature.

The mixture was then added to 250 µl of serum-free medium and incubated with the cells for at least 2 hours. The medium was finally removed and the cells were incubated for a period ranging from 24 hours to 7 days at a temperature of 37° C. in the presence of 5% $CO_2$.

The cells were harvested at 24 hours or at 48 hours after transfection and the *Renillia luciferase* and *Firefly luciferase* activities were analyzed with the Promega Dual Luc kit according the manufacturer's instructions. The activities were read on a Victor apparatus.

Example 6

Comparative Evaluation of the In Vitro Activity of the Polynucleotide

The relative activities of the CARP polynucleotide (pXL3634) and of the RSV (pXL3635) promoters were evaluated in vitro by transient transfection of primary cultures of rat cardiomyocytes and were expressed relative to the activity of the plasmid pRL-CMV (FIG. 5).

The results show that the polynucleotide upstream of the CARP gene (pXL3634) has a very low in vitro activity, on the order of 0.04% relative to that of the CMV promoter.

The relative activity of the nonspecific strong RSV promoter (pXL3635) was also low, respectively on the order of 0.05% and 0.68% of that of the reference CMV promoter.

Example 7

Construction of an Adenovirus

An adenovirus allowing the expression of the luciferase under the control of the CARP promoter was constructed according to the method of Crouzet et al. (*Proc. Natl. Acad. Sci. USA,* 94 (1997) 1414–1419), the expression cassette being identical to that of the plasmid pXL3634 (FIG. 3).

A shuttle vector allowing recombination in *Escherichia coli* was constructed in two stages. First, the CARP promoter (fragment: XhoI filled with Klenow/BamHI) was introduced into pXL3474 (digested with ScaI and BglII) between the regions ITR- and pIX in order to generate the plasmid pXL3758. Plasmid pXL3759 was then generated by introducing into pXL3758, which had been digested with BstBII (filled in with Klenow) and BstEII, the fragment containing the luciferase cDNA and the SV40 polyadenylation site (BamHI fragment filled with KIenow/BstEII of pXL3634). pXL3759 is schematically represented in FIG. 6A.

Homologous double recombination in *E. coli* was accomplished as described above, against a plasmid pXL3215 containing an E1/E3 adenoviral genome into which an RSV-LacZ expression cassette had been introduced into the E1 region. The plasmid pXL3215 is a derivative of the plasmid pXL2689, which contains the replication origin of the plasmid RK2, the tetracycline resistance gene (Crouzet et al. *Proc. Natl. Acad. Sci. USA,* 1997). The product of this double recombination, the plasmid pXL3778, was verified by sequencing of the expression cassette. After cleavage with PacI in order to release a linear viral genome, the plasmid was transfected into the Per.C6 cell line (WO 97/00326) in order to generate the virus AV1.0CARP-Luc+.

The virus was also verified by sequencing of the expression cassette and by restriction analysis. The presence of RCA E1+ (replication competent adenovirus) particles was tested for by hybridization with a probe.

Stocks with high virus titer were obtained by amplification of the virus in the Per.C6 line and the viral particles were purified on a CsCl gradient. The titer of this virus in viral particles/ml (vp/ml) was obtained by chromatography and its activity was checked in vitro by titration of the luciferase activity after infection of skeletal or cardiac muscle cells and comparison with a virus used as a control comprising a CMV promoter.

Example 8

Injection of DNA In Vivo

CD SPRAGUE rats weighing 200 g were anesthetized with a Ketamine (70 mg/ml)/Xylazine (6 mg/ml) mixture at 1 ml/kg injected by the intraperitoneal route.

The intramyocardiac injections were carried out after laparotomy by the transdiaphragmatic route with a 100 µl Hamilton glass syringe connected to a Steriflex catheter (ref. 167.10 G19 V) provided with a stop flange and ending with a BD 26G*3.8 needle (short bezel).

Fifty microliters of the DNA solution, adjusted to 0.9% of NaCl, were injected over 5 seconds.

After sacrificing the animals, the hearts were removed, rinsed in a 0.9% NaCl solution and macroscopically examined. They were then analyzed for luciferase activity using a kit (Promega E151A) after grinding with the aid of a homogenizer (Ultra-thurax, Diax600 Heidolph) in lysis buffer from the kit supplemented with protease inhibitors (Cmplete, Roche Diagnostics), followed by centrifugation for 20 minutes at 4000 rpm at 4° C. The readings were made on the apparatus LUMAT LB 9501 (10 µl of supernatant +50 µl of Promega luciferase substrate). Luciferase activities were converted to luciferase mass per heart (pg luciferase/heart) using the calibration described in Mir et al (*Proc. Natl. Acad. Sci. USA* 96 (1999), 4262–4267).

Alternatively, the hearts were fixed in 3.7% paraformaldehyde and analyzed by immunohistochemistry for the expression of FGF-1.

Example 9

Comparative Evaluation of the In Vivo Activity of the CARP Polynucleotide

The results presented in FIG. 7A show that the levels of expression of luciferase obtained upon injection of increasing doses 1, 5, 25 and 125 µg of plasmids pXL3031 and pXL3634 were not significantly different, thus, clearly demonstrating that the polynucleotide upstream of the CARP gene is capable of inducing high levels of expression equivalent to those of a strong promoter such as CMV.

On the other hand, the expression obtained with another strong viral promoter, the RSV promoter (pXL3635), was weaker than that obtained with either the CMV promoter or the polynucleotide upstream of the CARP gene (FIG. 7B).

Moreover, the addition of the CMV enhancer upstream of smooth muscle cell promoters (SM α-actin, pXL3130 or SM22, pXL3153) although demonstrated to be highly efficient in vitro (WO 00/18908) appeared to be ineffective in cardiac cells in vivo.

Example 10

Evaluation of the Specificity of Expression of the CARP Polynucleotide

25 µg of each of the plasmids pXL3634, pXL3435 and pXL3031 were administered to rats by intracardiac transdiaphragmatic injection.

In parallel, intramuscular injections were performed into the cranial tibial muscle of groups of mice with 10 µg of each of these plasmids with or without electrotransfer.

The expression of luciferase was analyzed 7 days after the injection as described (*Proc. Natl. Acad. Sci. USA* 96 (1999), 4262–4267).

The levels of expression of luciferase in the heart were expressed relative to the levels observed in the cranial tibial muscle, and are presented in FIG. 8.

The results clearly show that the polynucleotide upstream of the CARP gene and the CMV promoter were the only two promoters capable of inducing the highest expression in the cardiac tissue. However, the heart/muscle expression ratio was 1 with the CMV promoter, whereas this ratio was close to 100 when the polynucleotide upstream of the CARP gene was used, which clearly shows the very high selectivity of the latter for the cardiac tissue.

The superior specificity of the expression driven by the polynucleotide of the invention was also clear relative to other constructs comprising an enhancer and a promoter specific for smooth muscle cells such as that of the gene coding for the protein SM-22 and for actin for which the hearumuscle expression ratios are also presented in FIG. 8 by way of illustration.

We claim:

1. An isolated polynucleotide comprising SEQ ID NO: 1, wherein said polynucleotide comprises at least 92 nucleotides 3' to the transcription start position +1, and wherein said polynucleotide in the absence of inverted terminal repeat sequences from human adeno-associated virus specifically induces expression in cardiac cells in vivo of a gene which is operably linked to said polynucleotide.

2. An expression cassette comprising a sequence encoding a protein or an RNA of therapeutic interest operably linked to the polynucleotide according to claim 1.

3. The expression cassette according to claim 2, wherein the protein or RNA of therapeutic interest increases a rate of cardiac cell division, reduces or suppresses an immune response, induces angiogenesis, changes muscle contractility, reduces cardiac hypertrophy, reduces cardiac insufficiency, or reduces myocarditis.

4. The expression cassette according to claim 2, wherein the protein or RNA of therapeutic interest is a vascular endothelial growth factor, a fibroblast growth factor, an angiopoietin, or a cytokine.

5. The expression cassette according to claim 2, wherein the protein or RNA of therapeutic interest is an activating or an inhibiting transcription factor.

6. The expression cassette according to claim 2, wherein the protein is an immunosuppressive protein.

7. The expression cassette according to claim 6, wherein the immunosuppressive protein is interleukin-10, interleukin-2, or interleukin-8.

8. The expression cassette according to claim 2, wherein the RNA of therapeutic interest is an antisense RNA or a ribozyme.

9. The expression cassette according to claim 2, wherein the protein is nitric oxide synthetase, superoxide dismutase, or catalase.

10. A vector comprising the polynucleotide according to claim 1.

11. A vector comprising the expression cassette according to claim 2.

12. The vector according to claim 10, further comprising an origin of replication which is active in cardiac cells.

13. The vector according to claim 10, which is a plasmid or a cosmid.

14. The vector according to claim 10, which is or is derived from an adenovirus, a retrovirus, a herpesvirus, or an adeno-associated virus.

15. A composition comprising a therapeutically effective amount of the polynucleotide according to claim 1 and a pharmaceutically acceptable carrier.

16. A composition comprising a therapeutically effective amount of the vector according to claim 10 and a pharmaceutically acceptable carrier.

17. The vector according to claim 10, which is any DNA not encapsidated by viral proteins.

* * * * *

SEQUENCE LISTING

<160> NUMBER OF SEQ ID NOS: 5

<210> SEQ ID NO 1
<211> LENGTH: 2358
<212> TYPE: DNA
<213> ORGANISM: Mus musculus

<400> SEQUENCE: 1

```
ggatcctttc atgtttaaca atatcaaccc taacccaagg ggaacagcct gcctgacagt      60
ggctttgcca cccatgaata cttcctagtc tagtccgttt gtgaaactca gcccatccca     120
acacttctgc aagccccatc ctctacaagg tgctcattgg gaatttcctg gagcttctct     180
ttcaggatca gcctgattct agggcagcag ttctcaacct gggggcctcg accectttgg     240
```

```
gggaatcaaa cgacccttta caggggtcac atatcatcta tcctatatgt caggtattta      300
cattacgatt cgtaacagta gcaaaattac aggtatgaaa tagcaatgaa ataattttat      360
gattgaaggt caccacaaca tgaggccgcc acactgttct agagaaaaat cacctgggtg      420
gggaaaggtt tgggaaagcc tttctgtcca ttcttcattc ttcaaagtga tgtgttcaca      480
gaaagccttt cagctgttct gctgggctc ttagtaagtc tgagtaggaa ctgtatgtac       540
caggtctgct tcttatgggt ggagccaaga cgcatcgtgg gtggagcgaa gacgcaacct     600
caccttctag ctctgcatcc atagcaagta gcctaatgtt tctgtgtcta ggtgtcatct      660
ctgtgaatcg agatccttgg ccttgcttga attagggagg cacaaaatac tcagagattc      720
aagactgctc agcagcccag agtccttcct caaaggaaag gtctcaactc tcagcccccc      780
ttagctctga gtcaggcctg aacaaacgg ccacaggaat gagaaaagct gccatagctg      840
cttgtcactt caagaggtca agaaaatag tgttaaccat gaaaacgaga agaccaacag     900
ttatccattg atagcgtctc aggacagata ggacagagag aacactagga gagggaacc    960 cacgaaggac aagtattag tgtgttggtt ttcagggcaa tgtcttgtac tgaagattct      1020
agaaacacaa tttgctggtt gaacagctga agtgggtgg gggttcttac cccatgttca      1080
tggaagggtg agtgaggaga gacagatata tgatggccag cataacaaac atacacaaca     1140
ccctaattaa cacttccctc ttctactgac acccccttca ctctcctctt tcataaaaaa      1200 taaaaaagt attttatgtg gctcttacga tagaatcttt cctcgaacta taaaaagatc       1260
taaatattta tattttcac attttaatat cttagcgatg acaagccaga aacaagtatt       1320
ttttgcctct ctcaacagca aagcttgggg ccttttttgtt tccgtgttag aatagaaca     1380 cgagagcccc gtgtatctag gcagatgctc tatcattagc ccatgagtct ccagcctcag      1440
acgcacattt ttctcgggct ctcttaagct tttcccacag cattgggaaa ctttactgac       1500
agcatccaag ttgtgcttct gctaagaact ggactcacat ctctctgtgc atcacttcgg      1560
cccgttttgg ggtagatcct ctgattagcc ttcagattta gaacacggtg agcctgtggt      1620
gcactaatta tggccagtga caccatagag tcaaagtgca ttactgaatg ctttcaattt      1680
ctcctaatgc tggtacgatg gcatgtcaca gggccatttt agctgcagac atcactccag      1740
agaattccaa acagatagag acaagtggca cccagaccca tctccttccc ctcgggctga      1800
ttatccccag aaataggatg tcccaaagca acacttccca gccaactgga gtgctgataa      1860
gtccagttat cagaaagata tggctgtaag tgtgatgcac agtgcttgca ttttcttgat      1920
acgttagtca tatgagagct gacaaagaag gaaaaagagc agcgatgtgg tgcaatatta      1980
acaggcagct gtcccctggc ttcccgatac gtgggatgac tcgcattgct gagcggtgtg      2040
gtcactgcca aaggaatgac cctctcacat ttcttcctga ttcgcatacg ccgcggccag      2100
cttgtcatct ccctcttggg cttcccagac actaagtctg gaatgaaaat tcacctgcct      2160
ctgaattggc cactggtggg ggcaggggtg tgacttggct tcccaggctg aagattatc       2220 tcacccagcc ctagctatat aacgggctgg tgtggagggg ctccacaggg ccagttccag      2280
gggttcatcc acaagagaga aaaacataga ctcgaggtct agggagcttg catgcctgca      2340
ggtcggaggc caccatgg                                                    2358
```

<210> SEQ ID NO 2
<211> LENGTH: 2074
<212> TYPE: DNA
<213> ORGANISM: Homo sapiens

<400> SEQUENCE: 2

```
ctgcagcaag ttacttaatg ttttttgcct cagcatcctc tctgtaaaat gagagcatta      60
gtcttgctcc aacttcgagg gcatggacag ctctgggatt tcatatccaa gacccttaaa     120
catcccacag tccttccccc aaacacttct cctcctaata cctccctcag tttgggtcag     180
gcctggaaca aaaggcata cgaaatggta gaaaaagtgt ccatgactac ttctgactta      240
gatgaagaga ccaatgaaaa tagtaatgac tctgtttgct tcagcaggac atatactaaa    300
ataggagcta tacaaagaag attagcatgg actctgtgca agaatgacac acaaatttgt    360
gaaacattcc atatattaaa aataaataaa taataaagag aaaagaaaa aattaaaaag      420
aaaatagtga tagctgtgtc catctcaaag aaaagcccag gagatttcct ttatttaccc    480
cctttaagat agaatattag gagaccgaa catatgatac aggaggtact gggagggtcc     540
ctctttgtca atgttttgtc ttgggtgggg gagtcgatgt cttctcaaag tttcagaaac    600
accatccact gactgagcat tcaaggggca agaggagaat ggcagccaca tttgttgatt    660
gggtgagttt ggggagaaat agacacacaa aggtcaaaca taacttccta attaacactt    720
ccctccattc acaattccct tctcccattc ttctctcctg tcttttacts akaraaaccc    780
agttttcct gaaactataa aaatacccc agtatgttta cataatttac acctcaaaga      840
ttagaaacca gaaatagaga ccttttcaac ccttccggaa gcaaagtgca ttatccctcc    900
agccacgtgt ctcaaatctt gatgcatcag aatcatctgg gtgcttttkaa attcaagatg    960
attcctacga gttaccataa atcaactcag aattccctgg agtggggcca gggatctgta   1020
tttctgacaa gctcccacag gtgattcctt tccccacagc atttgagaac ttcagctcaa   1080
tgacctaatc agagtcctgc cattgctaat atctggtctc attttttbtca tatatatata   1140
tagtatttgt ggtagagatg ggattttgcc atgttgccca ggctagtatt gaactcctaa   1200
gctaagcaat cttcctgtct ctgcctccca aatgttggg attacaggtg taagccactg    1260
cacccggctg atagctggtt tcatttactc tatttcttga ccactctgat ccattttgaa   1320
gtaaaaatgc tccaattatt atgctgtttt agaacacggt aagcatgtca tgtgctaatg   1380
gccagtgaca tcataaaaga aaagtgcatt actgaatgct ttcaatgtct tataatgatg    1440
gtaaggtggc atgtcatggg gcctatttag cccagacatc actccaaaga attccaaaca   1500
gatatagaca agtgccttta gggcccagat cccttcccct caggctgttt acccagggaa   1560
taggatgtcc tgggacaagt ttcccctaag tgaagtgttg ataagtctgc ttatcagaaa    1620
gatattactg ggggtgtgat atgtagggca tctacatttt cttgataggt agtcatatga   1680
aagctgacaa agaaaaaaag ggcagtgatg tggtgcaatg tcaacagaca gctgtcccct   1740
gactcttgac aaataggatg acttgcattg ctgagcgatg tgatcaccac caaaggaatg    1800
gccctctcac atttcttcct gattcacata ttcagcaggg ttagcttgtc ctcccctccc   1860
tcttcagctt cccagacact gagtctggaa tgaaaattca cctgcctctg agttggctcc    1920
taatgggggc gggagtgtta cttcggttcc caggttggaa gattatctca cccggcccca   1980
gctatataag ctgaccggtg tggaggggcc cagcagggcc aactccaggg attccttcca    2040
cgacagaaaa acatacaaga ctccttcagc caac                                 2074
```

<210> SEQ ID NO 3
<211> LENGTH: 750
<212> TYPE: PRT
<213> ORGANISM: Homo sapiens

<400> SEQUENCE: 3

-continued

```
Met Gly Glu Thr Leu Gly Asp Ser Pro Ile Asp Pro Glu Ser Asp Ser
 1               5                  10                  15

Phe Thr Asp Thr Leu Ser Ala Asn Ile Ser Gln Glu Met Thr Met Val
                20                  25                  30

Asp Thr Glu Met Pro Phe Trp Pro Thr Asn Phe Gly Ile Ser Ser Val
            35                  40                  45

Asp Leu Ser Val Met Glu Asp His Ser His Ser Phe Asp Ile Lys Pro
         50                 55                  60

Phe Thr Thr Val Asp Phe Ser Ser Ile Ser Thr Pro His Tyr Glu Asp
 65                  70                  75                  80

Ile Pro Phe Thr Arg Thr Asp Pro Val Val Ala Asp Tyr Lys Tyr Asp
                 85                  90                  95

Leu Lys Leu Gln Glu Tyr Gln Ser Ala Ile Lys Val Glu Pro Ala Ser
                100                 105                 110

Pro Pro Tyr Tyr Ser Glu Lys Thr Gln Leu Tyr Asn Lys Pro His Glu
            115                 120                 125

Glu Pro Ser Asn Ser Leu Met Ala Ile Glu Cys Arg Val Cys Gly Asp
        130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
        195                 200                 205

Arg Phe Gly Arg Met Pro Gln Ala Glu Lys Glu Lys Leu Leu Ala Glu
        210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
                245                 250                 255

Thr Lys Ala Lys Ala Arg Ala Ile Leu Thr Gly Lys Thr Thr Asp Lys
            260                 265                 270

Ser Pro Phe Val Ile Tyr Asp Met Asn Ser Leu Met Met Gly Glu Asp
        275                 280                 285

Lys Ile Lys Phe Lys His Ile Thr Pro Leu Gln Glu Gln Ser Lys Glu
        290                 295                 300

Val Ala Ile Arg Ile Phe Gln Gly Cys Gln Phe Arg Ser Val Glu Ala
305                 310                 315                 320

Val Gln Glu Ile Thr Glu Tyr Ala Lys Ser Ile Pro Gly Phe Val Asn
                325                 330                 335

Leu Asp Leu Asn Asp Gln Val Thr Leu Leu Lys Tyr Gly Val His Glu
            340                 345                 350

Ile Ile Tyr Thr Met Leu Ala Ser Leu Met Asn Lys Asp Gly Val Leu
        355                 360                 365

Ile Ser Glu Gly Gln Gly Phe Met Thr Arg Glu Phe Leu Lys Ser Leu
        370                 375                 380

Arg Lys Pro Phe Gly Asp Phe Met Glu Pro Lys Phe Glu Phe Ala Val
385                 390                 395                 400

Lys Phe Asn Ala Leu Glu Leu Asp Asp Ser Asp Leu Ala Ile Phe Ile
                405                 410                 415
```

```
Ala Val Ile Ile Leu Ser Gly Asp Arg Pro Gly Leu Leu Asn Val Lys
                420             425                 430

Pro Ile Glu Asp Ile Gln Asp Asn Leu Leu Gln Ala Leu Glu Leu Gln
            435                 440                 445

Leu Lys Leu Asn His Pro Glu Ser Ser Gln Leu Phe Ala Lys Leu Leu
        450                 455                 460

Gln Lys Met Thr Asp Leu Arg Gln Ile Val Thr Glu His Val Gln Leu
465                 470                 475                 480

Leu Gln Val Ile Lys Lys Thr Glu Thr Asp Met Ser Leu His Pro Leu
                485                 490                 495

Leu Gln Glu Ile Tyr Lys Asp Leu Tyr Ala Trp Ala Ile Leu Thr Gly
            500                 505                 510

Lys Thr Thr Asp Lys Ser Pro Phe Val Ile Tyr Asp Met Asn Ser Leu
        515                 520                 525

Met Met Gly Glu Asp Lys Ile Lys Phe Lys His Ile Thr Pro Leu Gln
530                 535                 540

Glu Gln Ser Lys Glu Val Ala Ile Arg Ile Phe Gln Gly Cys Gln Phe
545                 550                 555                 560

Arg Ser Val Glu Ala Val Gln Glu Ile Thr Glu Tyr Ala Lys Ser Ile
                565                 570                 575

Pro Gly Phe Val Asn Leu Asp Leu Asn Asp Gln Val Thr Leu Leu Lys
            580                 585                 590

Tyr Gly Val His Glu Ile Ile Tyr Thr Met Leu Ala Ser Leu Met Asn
        595                 600                 605

Lys Asp Gly Val Leu Ile Ser Glu Gly Gln Gly Phe Met Thr Arg Glu
610                 615                 620

Phe Leu Lys Ser Leu Arg Lys Pro Phe Gly Asp Phe Met Glu Pro Lys
625                 630                 635                 640

Phe Glu Phe Ala Val Lys Phe Asn Ala Leu Glu Leu Asp Asp Ser Asp
                645                 650                 655

Leu Ala Ile Phe Ile Ala Val Ile Ile Leu Ser Gly Asp Arg Pro Gly
            660                 665                 670

Leu Leu Asn Val Lys Pro Ile Glu Asp Ile Gln Asp Asn Leu Leu Gln
        675                 680                 685

Ala Leu Glu Leu Gln Leu Lys Leu Asn His Pro Glu Ser Ser Gln Leu
690                 695                 700

Phe Ala Lys Leu Leu Gln Lys Met Thr Asp Leu Arg Gln Ile Val Thr
705                 710                 715                 720

Glu His Val Gln Leu Leu Gln Val Ile Lys Lys Thr Glu Thr Asp Met
                725                 730                 735

Ser Leu His Pro Leu Leu Gln Glu Ile Tyr Lys Asp Leu Tyr
            740                 745                 750

<210> SEQ ID NO 4
<211> LENGTH: 30
<212> TYPE: DNA
<213> ORGANISM: Artificial sequence
<220> FEATURE:
<223> OTHER INFORMATION: PCR Primer

<400> SEQUENCE: 4
ggcgatttaa ataatgtagt cttatgcaat                                    30

<210> SEQ ID NO 5
<211> LENGTH: 31
<212> TYPE: DNA
```

```
<213> ORGANISM: Artificial sequence
<220> FEATURE:
<223> OTHER INFORMATION: PCR Primer

<400> SEQUENCE: 5
ggggtctaga aggtgcacac caatgtggtg a                                              31
```